(12) United States Patent
Budzelaar et al.

(10) Patent No.: US 10,188,458 B2
(45) Date of Patent: Jan. 29, 2019

(54) INDUCTIVE DISTURBANCE REDUCTION DEVICE

(71) Applicant: KONINKLIJKE PHILIPS N.V., Eindhoven (NL)

(72) Inventors: Franciscus Paulus Maria Budzelaar, Elndhoven (NL); Szabolcs Deladi, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 425 days.

(21) Appl. No.: 14/782,813

(22) PCT Filed: Apr. 24, 2014

(86) PCT No.: PCT/EP2014/058298
§ 371 (c)(1),
(2) Date: Oct. 7, 2015

(87) PCT Pub. No.: WO2014/173990
PCT Pub. Date: Oct. 30, 2014

(65) Prior Publication Data
US 2016/0066987 A1 Mar. 10, 2016

(30) Foreign Application Priority Data

Apr. 24, 2013 (EP) .................................... 13165037

(51) Int. Cl.
*A61B 18/14* (2006.01)
*A61B 17/00* (2006.01)
(Continued)

(52) U.S. Cl.
CPC ..................... *A61B 18/1492* (2013.01); *A61B 2017/00526* (2013.01); *A61B 2018/00178* (2013.01);
(Continued)

(58) Field of Classification Search
CPC . A61B 18/14; A61B 18/1442; A61B 18/1445; A61B 18/1448; A61B 18/1492;
(Continued)

(56) References Cited

U.S. PATENT DOCUMENTS 5,967,853 A 10/1999 Hashim
6,018,447 A * 1/2000 Hannah ................ H05K 9/0064
361/103

(Continued)

FOREIGN PATENT DOCUMENTS

DE 102010061955 A1 5/2012
EP 0708501 A1 4/1996

*Primary Examiner* — Jaymi Della
*Assistant Examiner* — Khadijeh Vahdat

(57) ABSTRACT

The invention relates to an inductive disturbance reduction device (18) for reducing an inductive disturbance of a signal like an ultrasound signal to be transmitted via first connection conductors (25, 26) of an electrical connector (11), which is caused when ablation current flows through a second connection conductor (24) of the electrical connector. The inductive disturbance reduction device is adapted to induce a voltage, which at least partly compensates a voltage induced in the electrical connector, in order to reduce the inductive disturbance in the signals to be transmitted via the first connection conductors of the electrical connector. Since the inductive disturbance is reduced, a high quality electrical connection can be provided, without necessarily using, for instance, a technically relatively complex and expensive coaxial connector. The inductive disturbance reduction device may be integrated, for instance, in a part of the electrical connector or in a cable.

14 Claims, 6 Drawing Sheets

(51) Int. Cl.
*A61B 18/00* (2006.01)
*A61B 90/00* (2016.01)

(52) U.S. Cl.
CPC . *A61B 2090/376* (2016.02); *A61B 2090/3784* (2016.02); *H01R 2201/12* (2013.01)

(58) Field of Classification Search
CPC ........... A61B 2018/00178; A61B 2017/00526; A61B 2090/376; A61B 2090/3784; H01R 2201/12
USPC .................. 606/27–50; 361/42, 103–115
See application file for complete search history.

(56) References Cited

U.S. PATENT DOCUMENTS

| | | |
|---|---|---|
| 8,784,321 B2 | 7/2014 | Courtney et al. |
| 9,039,698 B2 | 5/2015 | Ormsby et al. |
| 2004/0087939 A1 | 5/2004 | Eggers et al. |
| 2004/0225210 A1 | 11/2004 | Brosovich et al. |
| 2006/0028780 A1* | 2/2006 | Pessl ................ H01L 23/60 361/111 |
| 2008/0233806 A1 | 9/2008 | Rothermel et al. |
| 2012/0161893 A1* | 6/2012 | Ye ...................... H01P 3/026 333/5 |
| 2013/0231655 A1 | 9/2013 | Budzelaar et al. |
| 2014/0091873 A1 | 4/2014 | Ye |

* cited by examiner

INDUCTIVE DISTURBANCE REDUCTION DEVICE

CROSS-REFERENCE TO PRIOR APPLICATIONS

This application is the U.S. National Phase application under 35 U.S.C. § 371 of International Application Serial No. PCT/EP2014/058298, filed on Apr. 24, 2014, which claims the benefit of EP Application Serial No. 13165037.6, filed on Apr. 24, 2013. These applications are hereby incorporated by reference herein.

FIELD OF THE INVENTION

The invention relates to an inductive disturbance reduction device for reducing an inductive disturbance of a signal to be transmitted via first connection conductors of an electrical connector, which is caused when current flows through a second connection conductor of the electrical connector. The invention relates further to an electrical connector comprising the inductive disturbance reduction device and a cable comprising the inductive disturbance reduction device. The invention also relates to a manufacturing apparatus and a manufacturing method for manufacturing the inductive disturbance reduction device.

BACKGROUND OF THE INVENTION

In many minimal invasive interventions multipurpose catheters are used, in which treatment and monitoring functionalities are integrated. One example of such a multipurpose catheter is an ablation catheter comprising a radio frequency (RF) ablation tip and sensitive ultrasound elements, i.e. ultrasound transducers, which may be used for monitoring, for instance, lesion depth in real-time. The ablation catheter comprises a high current ablation wire for conducting RF ablation current from an external ablation current source to the tip of the ablation catheter and signal wires for transmitting ultrasound signals from the ultrasound elements arranged at the tip of the ablation catheter to an external ultrasound control unit. Within the ablation catheter the high current ablation wire and the signal wires are generally well shielded from each other such that the magnetic field generated by the high current flowing through the high current ablation wire does not induce a significant induction voltage within the signal wires. However, an electrical connector is used for electrically connecting the high current ablation wire and the signal wires to the ablation current source and the ultrasound control unit, respectively, wherein within the electrical connector the signal wires are often less shielded from the magnetic field generated by the high ablation current flowing through the high current ablation wire, which may lead to induced voltages in the signal wires that interfere with the ultrasound signals to be transmitted and therefore diminish the quality of the transmitted ultrasound signals.

WO 99/27627 discloses an apparatus comprising a capacitor gasket defining a through hole, a conductive plate coupled adjacent to the capacitor gasket and in electrical contact with a plurality of capacitors of the capacitor gasket, and a pair of conductive contacts each having a thin region, wherein the conductive contacts are coupled to a differential pair of signal lines. WO 2012/087956 A2 discloses an apparatus comprising a first differential signal pair and a second differential signal pair, wherein the second differential signal pair is located near the first differential signal pair and switches polarity near a middle point of a routing length of the second differential signal pair.

WO 2011/066445 A2 discloses an RF ablation system comprising an ablation catheter with a hollow conductive coaxial cable, a connector at a proximal end of the cable and an ablation member a distal end of the cable configured to apply RF energy to a target tissue site. The cable has a first inner elongated electrically conductive tubular member having an axially extended lumen or passageway, a second elongated outer electrically conductive member disposed in a substantially coaxial relationship over at least a portion of the first electrically conductive tubular member, a dielectric medium between the inner and outer conductive tubular members, and an electromagnetic (EM) tracking sensor located at the distal end of the cable. The RF ablation system further comprises an EM field generator for generating an EM field which induces a voltage in the EM tracking sensor when the EM tracking sensor is within the generated EM field and a signal processing unit with a signal processor connected to the connector at the proximal end of the cable, wherein the EM tracking sensor communicates with the signal processor and the signal processor is configured to detect an induced voltage in the EM tracking sensor and to determine the position and orientation of the distal end of the ablation catheter in a patient's body using the induced voltage.

SUMMARY OF THE INVENTION

It is an object of the present invention to provide an inductive disturbance reduction device for reducing an inductive disturbance of a signal to be transmitted via first connection conductors of an electrical connector, which is caused when current flows through a second connection conductor of the electrical connector. It is a further object of the present invention to provide an electrical connector comprising the inductive disturbance reduction device and a cable comprising the inductive disturbance reduction device. It is also an object of the present invention to provide a manufacturing apparatus and a manufacturing method for manufacturing the inductive disturbance reduction device.

In a first aspect of the present invention an inductive disturbance reduction device is presented, wherein the inductive disturbance reduction device is adapted to reduce an inductive disturbance of a signal to be transmitted via first connection conductors of an electrical connector, which is caused when RF ablation current usable for ablating tissue flows through a second connection conductor of the electrical connector, wherein the electrical connector is adapted to electrically connect an ablation catheter with an RF ablation current source and wherein the inductive disturbance reduction device comprises:

first conductors for being electrically connected to the first connection conductors of the electrical connector for transmitting the signals, and a second conductor for being electrically connected to the second connection conductor of the electrical connector for transmitting the current, wherein the first conductors and the second conductor of the inductive disturbance reduction device are arranged such that in the first conductors of the inductive disturbance reduction device a voltage is induced, when the current flows through the first conductor of the inductive disturbance reduction device, which at least partly compensates a voltage induced in the first connection conductors of the electrical connector, when the current flows through the second connection conductor of the electrical connector.

Since in the inductive disturbance reduction device a voltage is induced, which at least partly compensates a voltage induced in the electrical connector, i.e. since voltages are induced having opposite polarities such that they at least partly cancel each other out, the overall induced voltage is reduced, in particular, eliminated, which in turn leads to a reduced inductive disturbance in the signals to be transmitted via the first connection conductors of the electrical connector.

The electrical connector may comprise two or more first connection conductors for transmitting signals and a single second connection conductor for transmitting the current, particularly two or more wires for conducting the electrical signals and one wire for conducting the current.

The electrical connector may be adapted to connect two cables, wherein each cable includes a coaxial cable for transmitting the signals and one wire for transmitting the current. The electrical connector can be adapted to electrically connect the coaxial cables, without using a coaxial connector, wherein nevertheless the transmitted signals are not significantly disturbed, because of the arrangement of the conductors in the inductive disturbance reduction device. Thus, a high quality electrical connection can be provided, without necessarily using a technically relatively complex and expensive coaxial connector.

The electrical connector is adapted to electrically connect an ablation catheter with an RF ablation current source, wherein the second conductor of the inductive disturbance reduction device is adapted to transmit RF ablation current usable for ablating tissue. Moreover, the first conductors of the inductive disturbance reduction device are preferentially adapted to transmit ultrasound sensing signals. Thus, the electrical connector can be adapted to electrically connect an ablation catheter comprising an ablation electrode and an ultrasound transducer at its tip with an ablation current source and an ultrasound control unit, wherein the ultrasound signals are not significantly disturbed by interferences caused by the magnetic field generated, when RF ablation current is flowing through the second connection conductor, without necessarily requiring, for instance, a coaxial connector.

In an embodiment at least one of the first connection conductors of the electrical connector is closer to the second connection conductor of the electrical connector than another of the first connection conductors of the electrical connector, wherein a first conductor of the first conductors of the inductive disturbance reduction device for being electrically connected to a first connection conductor of the electrical connector, which is closer to the second connection conductor of the electrical connector, is farther away from the second conductor of the inductive disturbance reduction device than another first conductor of the inductive disturbance reduction device for being electrically connected to a first connection conductor of the electrical connector, which is farther away from the second connection conductor of the electrical connector. In particular, the first connection conductors and the second connection conductor of the electrical connector may be at least partly straight, wherein the first conductors and the second conductor of the inductive disturbance reduction device may be at least partly straight and wherein a straight part of the first conductor of the first conductors of the inductive disturbance reduction device for being electrically connected to a straight part of the first connection conductor of the electrical connector, which is closer to a straight part of the second connection conductor of the electrical connector, may be farther away from a straight part of the second conductor of the inductive disturbance reduction device than a straight part of another first conductor of the first conductors of the inductive disturbance reduction device for being electrically connected to a straight part of a first connection conductor of the electrical connector, which is farther away from a straight part of the second connection conductor of the electrical connector. Thus, the electrical connector can be, for instance, an available, technically relatively simple and not very expensive standard non-coaxial electrical connector or a part of this non-coaxial connector and in the inductive disturbance reduction device the first connection conductors may be twisted. Such a combination of an electrical connector and the inductive disturbance reduction device can therefore be provided in a technically relatively simple way.

In an embodiment the inductive disturbance reduction device is integrated in or connected to the electrical connector. In particular, the electrical connector comprises first and second separate parts, which are connectable for electrically connecting first conductors for transmitting signals and second conductors for transmitting current, wherein the inductive disturbance reduction device is integrated in or connected to one of the first and second parts. For instance, the first part may be a straight conductors connector component in which all of the first connection conductors and the second connection conductor are straight along their entire length, wherein the second part forming the inductive disturbance reduction device may be a non-straight conductors connector component in which not all of the first conductors and the second conductors are straight along their entire length. For example, the first and second parts may be adapted such that they are separate components, which are engageable for electrically connecting electrical devices with each other. For instance, one of the first and second parts can form a male member and the other of the first and second parts can form a female member, in order to provide engageable first and second parts. The first part may be connected to a first electrical device, i.e. directly or via a cable, and the second part may be electrically connected to a second electrical device, i.e. directly or via a cable, wherein then the first and second electrical devices can easily be electrically connected by engaging the first and second parts of the electrical connector with each other.

In a further embodiment the inductive disturbance reduction device is integrated with a cable comprising first conductors for transmitting signals and a second conductor for transmitting current, wherein the cable is adapted to be connected to the electrical connector or wherein the cable is connected to the electrical connector. The inductive disturbance reduction device can be located at an end of the cable or in between the ends of the cable. If such a cable is electrically connected to the electrical connector, the overall voltage induced in the electrical connector and in the cable with the inductive disturbance reduction device will be reduced, in particular, eliminated.

The first conductors and the second conductor of the inductive disturbance device may be overmolded for forming an overmolded component as the inductive disturbance reduction device. However, the inductive disturbance reduction device may also be manufactured in another way. For instance, the inductive disturbance reduction device may be manufactured by using a printed circuit board or a flexible foil on which the first conductors and the second conductor of the inductive disturbance reduction device are arranged. For instance, the inductive disturbance reduction device can comprise a printed circuit board with the arrangement of the first conductors and the second conductor, wherein the printed circuit board can be soldered to the electrical connector. In particular, the printed circuit board can comprise a trace forming the second conductor of the inductive disturbance reduction device and traces forming the first conductors of the inductive disturbance reduction device, wherein the traces are laid out such that the voltage induced in the inductive disturbance reduction device has a polarity being opposite to the polarity of a voltage induced in the electrical connector. If the first conductors and the second conductor of the inductive disturbance reduction device are arranged on a flexible foil, the flexible foil is preferentially arranged on a rigid support means. For instance, it may be fixed in a handset of a catheter, if the electrical connector is used for connecting a catheter to other electrical devices like an RF ablation current source and one or several monitoring units like an ultrasound monitoring unit.

In another aspect of the present invention an electrical connector being adapted to electrically connect an ablation catheter with an RF ablation current source is presented, which comprises:

first connection conductors for electrically connecting first conductors for transmitting signals, a second connection conductor for connecting second conductors for transmitting RF ablation current usable for ablating tissue, wherein in the first connection conductors a voltage is induced, when current flows through the second connection conductor, an inductive disturbance reduction device as described above.

In a further aspect of the present invention a cable is presented, wherein the cable comprises first conductors for transmitting signals and a second conductor for transmitting RF ablation current usable for ablating tissue, wherein the cable is adapted to be connected to an electrical connector or wherein the cable is connected to the electrical connector, wherein the electrical connector is adapted to electrically connect an ablation catheter with an RF ablation current source and wherein the electrical connector comprises first connection conductors for electrically connecting the first conductors of the cable for transmitting the signals and a second connection conductor for electrically connecting the second conductor of the cable for transmitting the current, wherein in the first connection conductors a voltage is induced, when current flows through the second connection conductor. The cable further comprises an inductive disturbance reduction device as described above.

In a further aspect of the present invention a manufacturing apparatus is presented, wherein the manufacturing apparatus is adapted to manufacture an inductive disturbance reduction device (as described above) for reducing an inductive disturbance of a signal to be transmitted via first connection conductors of an electrical connector, which is caused when RF ablation current usable for ablating tissue flows through a second connection conductor of the electrical connector, wherein the electrical connector is adapted to electrically connect an ablation catheter with an RF ablation current source and wherein the manufacturing apparatus comprises:

an electrical conductor providing unit for providing first conductors of the inductive disturbance reduction device for being electrically connected to the first connection conductors of the electrical connector for transmitting the signals and a second conductor of the inductive disturbance reduction device for being electrically connected to the second connection conductor of the electrical connector for transmitting the current, an arranging unit for arranging the first conductors and the second conductor of the inductive disturbance reduction device such that in the first conductors of the inductive disturbance reduction device a voltage is induced, when the current flows through the first conductor of the inductive disturbance reduction device, which at least partly compensates a voltage induced in the first connection conductors of the electrical connector, when the current flows through the second connection conductor of the electrical connector.

In another aspect of the present invention a manufacturing method is presented, the manufacturing method is adapted to manufacture an inductive disturbance reduction device as described above for reducing an inductive disturbance of a signal to be transmitted via first connection conductors of an electrical connector, which is caused when RF ablation current usable for ablating tissue flows through a second connection conductor of the electrical connector, wherein the electrical connector is adapted to electrically connect an ablation catheter with an RF ablation current source and wherein the manufacturing method comprises:

providing first conductors of the inductive disturbance reduction device for being electrically connected to the first connection conductors of the electrical connector for transmitting the signals and a second conductor of the inductive disturbance reduction device for being electrically connected to the second connection conductor of the electrical connector for transmitting the current by an electrical conductor providing unit, arranging the first conductors and the second conductor of the inductive disturbance reduction device such that in the first conductors of the inductive disturbance reduction device a voltage is induced, when the current flows through the first conductor of the inductive disturbance reduction device, which at least partly compensates a voltage induced in the first connection conductors of the electrical connector, when the current flows through the second connection conductor of the electrical connector, by an arranging unit.

It shall be understood that the inductive disturbance reduction device, the electrical connector, the cable, the manufacturing apparatus, and the manufacturing method have similar and/or identical preferred embodiments, in particular, as defined herein.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
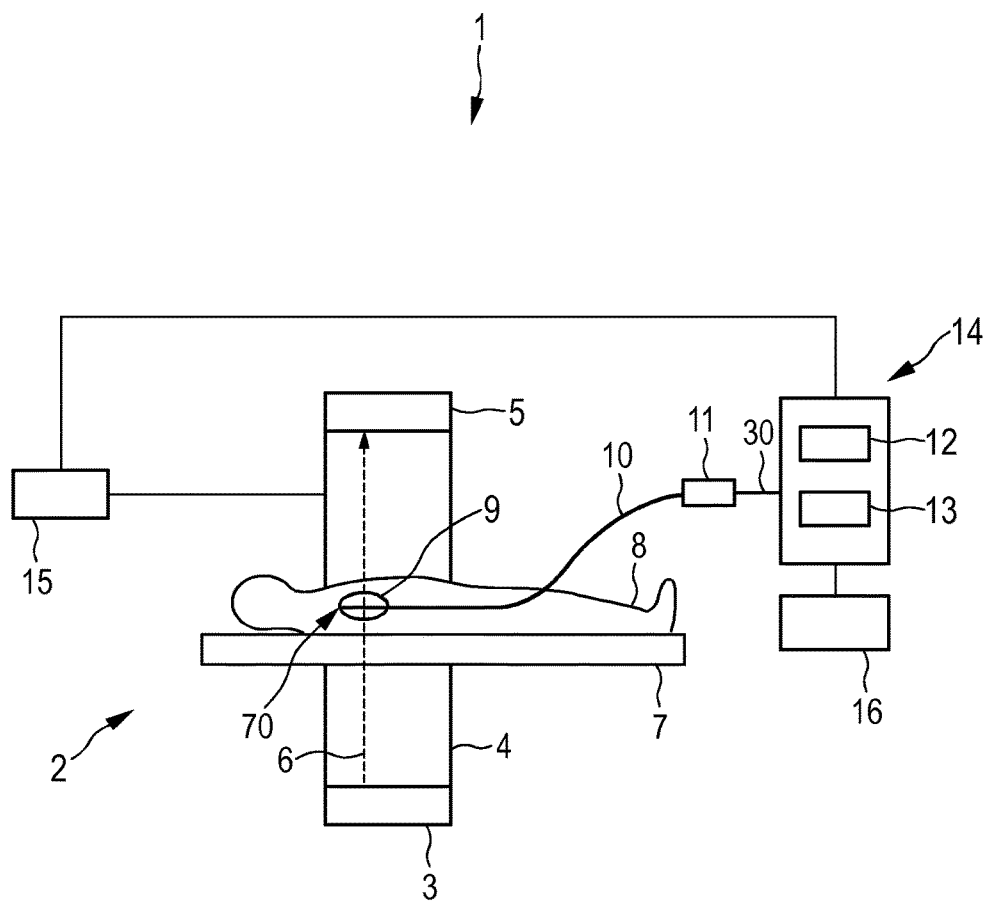
FIG. 1 shows schematically and exemplarily an embodiment of a system for performing an ablation procedure.

FIG. 1 shows schematically and exemplarity an embodiment of an ablation system for performing an ablation procedure. The ablation system 1 comprises an ablation catheter 10 for ablating a target region within a person 8 arranged on a support means like a patient table 7. In this embodiment the distal tip of the ablation catheter 10 has been introduced into the heart 9 of the person 8 for ablating cardiac tissue at different locations within the heart 9.

A fluoroscopy device 2 is used for imaging the distal tip of the ablation catheter 10 within the person 8 during the interventional procedure. The fluoroscopy device 2 comprises an x-ray source 3 for emitting x-rays 6 traversing the person 8 lying on the patient table 7. The fluoroscopy device 2 further comprises an x-ray detector 5 for detecting the x-rays 6, after having traversed the person 8. The x-ray source 3 and the x-ray detector 5 are mounted on a C-arm 4, which is rotatable with respect to the person 8, in order to irradiate the person 8 in different directions. Moreover, the support means 7 and the C-arm 4 may be translatable with respect to each other, in order to irradiate different parts of the person 8. The x-ray detector 5 is adapted to generate detection signals being indicative of the detected x-rays 6, wherein the detection signals are transmitted to a fluoroscopy control unit 15, which is adapted to control the C-arm 4, the x-ray source 3 and the x-ray detector 5 and to generate two-dimensional projection images depending on the received detection signals. The two-dimensional projection images may be shown on a display 16.

Figure 2:
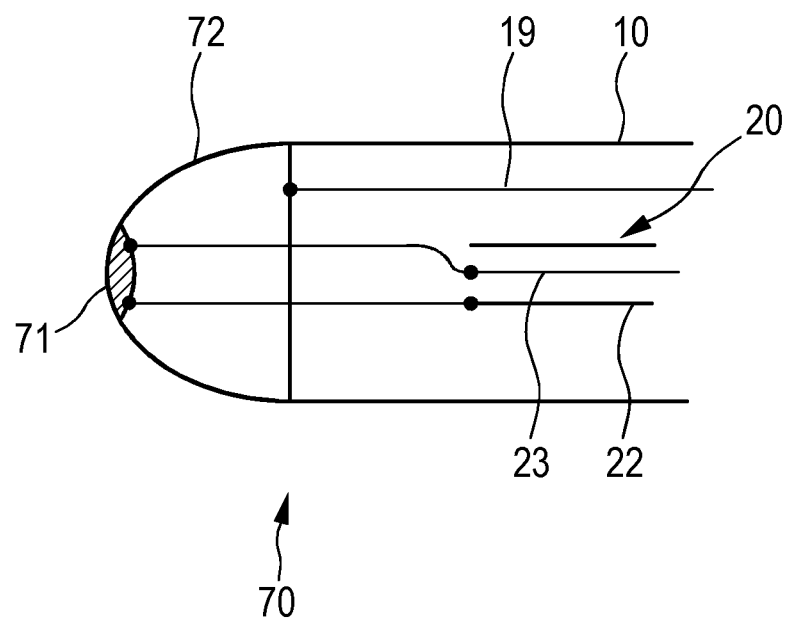
FIG. 2 shows schematically and exemplarily a tip of an ablation catheter used during the ablation procedure, FIG. 3 schematically and exemplarily illustrates an electrical connector with an integrated inductive disturbance reduction device, FIG. 4 schematically and exemplarily illustrates connection regions of the electrical connector, FIG. 5 schematically and exemplarily illustrates an electrical connector and a cable with an inductive disturbance reduction device.

The ablation catheter 10 comprises at its distal tip 70 an ablation electrode 72 and an ultrasound transducer 71 as schematically and exemplarily illustrated in FIG. 2. The ablation electrode 72 is electrically connected to a second conductor 19, which may be regarded as being an ablation current conductor 19, and the ultrasound transducer 71 is electrically connected to first conductors 22, 23 of a coaxial cable 20, which may be regarded as being signal conductors.

The ablation catheter 10 is electrically connected with an ultrasound control unit 12 and an ablation current source 13 via an electrical connector 11, wherein the ultrasound control unit 12 and the ablation current source 13 may be arranged in a same device 14 or they may be separately arranged. The ultrasound control unit 12 is adapted to receive ultrasound signals from the ultrasound transducer 71 and to generate ultrasound images based on the received ultrasound signals, which are shown on the display 16. The ultrasound control unit 12 is further adapted to control the ultrasound transducer 71 by sending control signals to the ultrasound transducer 71. The ablation current source 13 is adapted to provide RF ablation current to the ablation electrode 72 for ablating tissue within the person 8.

Figure 3:
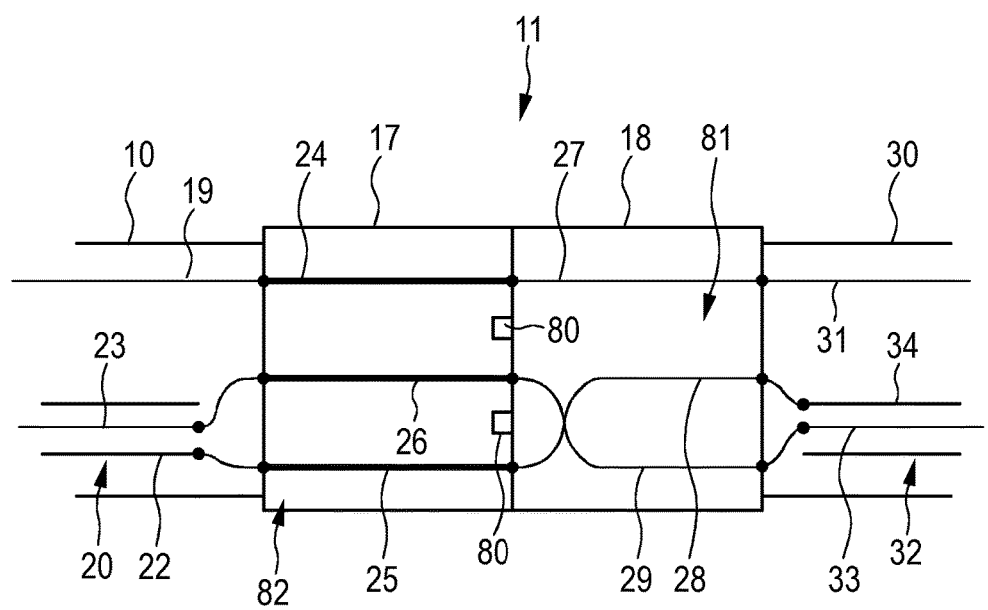

The electrical connector 11 is schematically and exemplarily illustrated in more detail in FIG. 3. The electrical connector 11 is adapted to electrically connect the first conductors 22, 23 of the coaxial cable 20 with first conductors 33, 34 of a further coaxial cable 32 connected with the device 14, in order to transmit the ultrasound signals to the device 14, especially to the ultrasound control unit 12. The electrical connector 11 is further adapted to electrically connect the second conductor 19 of the ablation catheter 10 with a second conductor 31, which may be regarded as being an ablation current conductor, for providing the RF ablation current from the RF ablation current source 13. The second conductor 31 and the further coaxial cable 32 are located in a cable 30.

The electrical connector 11 comprises a first part 17 and a second part 18. The first part 17 includes a second connection conductor 24 connected to the second conductor 19 of the ablation catheter 10 and first connection conductors 25, 26 connected to the first conductors 22, 23 of the ablation catheter 10. The second part 18 of the electrical connector 11 forms an inductive disturbance reduction device for reducing an inductive disturbance of a signal to be transmitted via the first connection conductors 25, 26 of the electrical connector 11, which is caused when current flows through the second connection conductor 24 of the electrical connector 11. The second part 18 comprises a second conductor 27 connected to the second conductor 31 of the cable 30 and first conductors 28, 29 connected to the first conductors 33, 34 of the cable 30.

In the first part 17 of the electrical connector 11 the first connection conductors 25, 26 and the second connection conductor 24 are arranged such that a first induction voltage is induced in the first connection conductors 25, 26, when current flows through to the second connection conductor 24, and in the second part 18 of the electrical connector 11 the first conductors 28, 29 and the second conductor 27 are arranged such that a second induction voltage is induced in the first conductors 28, 29, when current flows through the second conductor 27, which at least partly compensates the first induction voltage.

The first connection conductors 25, 26 and the second connection conductor 24 of the first part 17 are embedded in insulating material 82 and the first conductors 28, 29 and the second conductor 27 of the second part 18 are embedded in insulating material 81. In this embodiment, the first and second parts 17, 18 are adapted such that they are separate components, which are engageable for electrically connecting the ablation catheter 10 to the device 14. In particular, the second part 18 can be a male component comprising protrusions 80 for being received by corresponding depressions in the first part 17 forming a female component. In FIG. 3 the first and second parts 17, 18 are shown in an engaged state.

In the first part 17 all of the first connection conductors 25, 26 and the second connection conductor 24 are straight along their entire lengths. They can be formed by straight pins. The first part 17 can be regarded as being a straight conductor connector component. It can be, for instance, a standard non-coaxial electrical connector component.

In the second part 18 the first conductors 28, 29 are twisted. This leads to a configuration in which the first conductor 29 of the second part 18, i.e. of the inductive disturbance reduction device 18, which is electrically connected to the first connection conductor 26 of the first part 17, which is closer to the second connection conductor 24 of the electrical connector 11 than the first connection conductor 25, is farther away from the second conductor 27 of the second part 18 than the other first conductor 28 of the second part 18, which is electrically connected to the first connection conductor 25 of the first part 17, which is farther away from the second connection conductor 24 of the first part 17. This configuration leads to oppositely directed induced voltages in the first and second parts 17, 18 such that the overall induced voltage is reduced in the first connection conductors 25, 26 of the first part 17 and the first conductors 28, 29 of the second part 18.

In a further embodiment the second part 18 can be a printed circuit board with traces forming the second conductor 27 and the first conductors 28, 29, respectively. This second part 18 formed by a printed circuit board with traces can be soldered to the first part 17 such that the electrical configuration described above with reference to FIG. 3 is provided, in order to induce an induction voltage in the first conductors 28, 29 of the second part 18, which at least partly cancels out an induction voltage induced in the first connection conductors 25, 26 of the first part 17. In a further embodiment the second part 18 may be formed by a flexible foil on which the first and second conductors 27, 28, 29 of the second part 18 can be arranged as schematically and exemplarily shown in FIG. 3. The flexible foil can be arranged on a rigid support means like a handset of the ablation catheter 10. The second part 18 forming the inductive disturbance reduction device is attached to the cable 30. Thus, the inductive disturbance reduction device 18 can not only be regarded as being integrated with the electrical connector 11, but it can also be regarded as being integrated with the cable 30.

Figure 4:
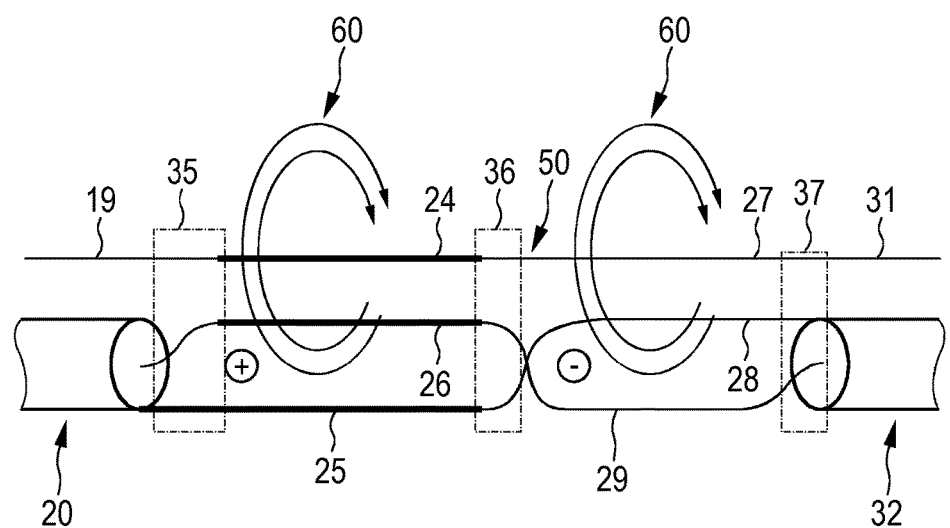

FIG. 4 schematically and exemplarily illustrates connection regions 35, 36, 37, in which different components are electrically connected to each other. In these connection regions 35, 36, 37 wires or other electrical conductors may be arranged in a not very controlled way such that electrical signals may be induced in these connection regions, which may not be completely compensated. They are therefore preferentially as small as possible, in order to reduce variations of interference magnitude from component to component. Preferentially, these regions are sized such that the voltage induced in these regions is less than 10 percent of the voltage induced in the first connection conductors 25, 26 of the first part 17 of the electrical connector 11. In an embodiment these connection regions each have a length being smaller than 5 mm. FIG. 4 further illustrates the magnetic field 60 generated by the current flowing through the second connection conductor 24 of the first part 17 and through the second conductor 27 of the second part 18.

Figure 5:
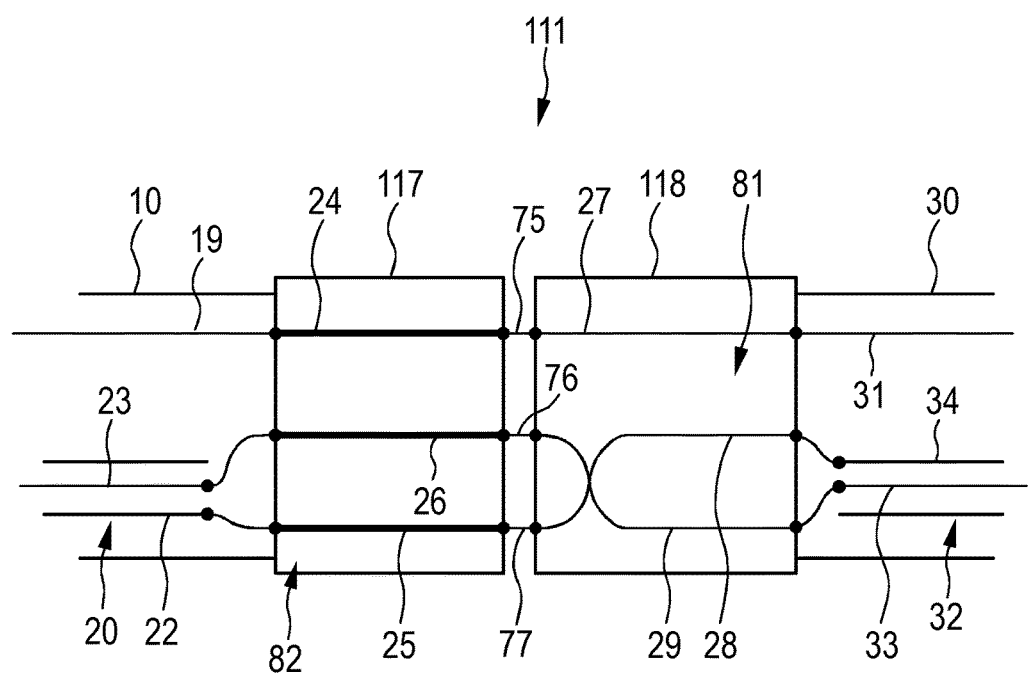

FIG. 5 schematically and exemplarily shows an embodiment of an electrical connector 111 comprising a first part 117 which is separated from a second part 118 forming an inductive disturbance reduction device. The arrangement of the electrical conductors in the first and second parts 117, 118 is similar to the arrangement described above with reference to FIG. 3. However, in this embodiment the second connection conductor 24 of the first part 117 and the second conductor 27 of the second part 118 are connected via an intermediate connecting conductor 75 and the first connection conductors 25, 26 of the first part 117 and the first conductors 28, 29 are connected via intermediate connecting conductors 77, 76. The intermediate connecting conductors 75, 76, 77 may be provided by soldering the second part 118 to the first part 117. In this embodiment the second part 118 is preferentially formed by a printed circuit board or a flexible foil on a rigid support means, wherein on the printed circuit board or on the flexible foil the first and second conductors 27, 28, 29 of the second part 118 are provided.

Figure 6:
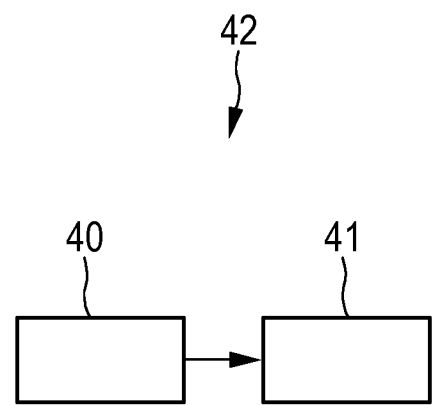
FIG. 6 shows schematically and exemplarily an embodiment of a manufacturing apparatus for manufacturing an inductive disturbance reduction device.

In the following an embodiment of a manufacturing apparatus for manufacturing the inductive disturbance reduction device 18 will be described with reference to FIG. 6. The manufacturing apparatus 42 comprises an electrical conductor providing unit 40 for providing the first conductors 28, 29 and the second connection conductor 27 to be used by the inductive disturbance reduction device 18. The manufacturing apparatus 42 further comprises an arranging unit 41 for forming the inductive disturbance reduction device 18 by arranging the first conductors 28, 29 and the second conductor 27 such that a voltage is induced in the first conductors 28, 29, if the inductive disturbance reduction device 18 is electrically connected with the first part 17 of the electrical connector 11 and when current flows through the second conductor 27 of the inductive disturbance reduction device 18, which at least partly compensates an induction voltage induced in the first connection conductors 25, 26 of the first part 17. The manufacturing apparatus may be further adapted to also produce the first part 17. However, the first part 17 may also be an already available non-coaxial electrical connector, which may be electrically connected to the produced second part 18, i.e. to the inductive disturbance reduction device 18, for providing the electrical connector 11. Instead of producing the second part 18 described above with reference to FIG. 3, the arranging unit 41 can also be adapted to arrange the conductors on a printed circuit board or a flexible foil.

Figure 7:
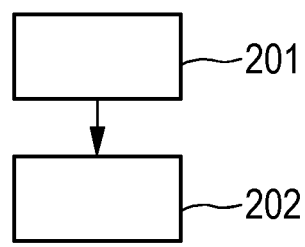
FIG. 7 shows a flowchart exemplarily illustrating an embodiment of a manufacturing method for manufacturing an inductive disturbance reduction device.

In the following a manufacturing method for manufacturing the inductive disturbance reduction device 18 will exemplarily be described with reference to a flowchart shown in FIG. 7.

In this embodiment the manufacturing method is adapted to produce the second part 18, i.e. the inductive disturbance reduction device 18, of the electrical connector 11 only. However, in another embodiment the manufacturing method can be further adapted to also produce the first part 17 of the electrical connector 11. In step 201 the first conductors 28, 29 and the second conductor 27 are provided by the electrical conductor providing unit 40. In step 202 the second part 18 of the electrical connector is formed, wherein the first conductors 28, 29 and the second conductor 27 are arranged such by the arranging unit 41 that voltage is induced in the first conductors 28, 29, if the second part 18 is electrically connected to the first part 17 and when current is flowing through the second conductor 27, which at least partly compensates a voltage induced in the first connection conductors 25, 26 of the first part 17.

In many minimal invasive interventions multipurpose catheters are used, in which treatment and monitoring functionalities are integrated. One example of such a multipurpose catheter is the above described ablation catheter 10 comprising an RF ablation tip and one or several sensitive ultrasound elements, i.e. ultrasound transducers, which may be used for monitoring, for instance, lesion depth in real-time. However, in known catheters this integration of treatment and monitoring functionalities introduce problems in the form of interference. Especially the presence of high power ablation signals, i.e. high power ablation currents, close to ultrasound channels may degrade the performance of the ultrasound signals. This situation is even worse, if low cost connectors are used. Coaxial connectors would be a good choice from an electrical point of view, but they are technically relatively complex and therefore relatively expensive. Known non-coaxial connectors implicate that each pair of unshielded pins, which are used to carry an ultrasound signal, form a loop, which makes the ultrasound signal transmitting channel sensitive to magnetic fields created by a high current ablation wire. Thus, if ultrasound signal carrying wires and a high current ablation wire are combined in a known non-coaxial connector, interference will be induced. Moreover, if the non-coaxial connector only comprises a single ablation current wire, as it is generally the case in ablation applications where the non-coaxial connector would only carry the forward current path, while the return path is via a different route, a non-zero total current will flow through the cable assembly such that magnetic fields are unavoidable.

The electrical connector described above with reference to, for instance, FIG. 3 is therefore adapted to introduce an additional interference on purpose, which has the opposite polarity, in order to cancel the perceived interference. Preferentially two signal conductors, i.e. two signal wires, are used for forming a sensitive signal path, and one current conductor, in particular, one ablation wire, is preferentially used to carry high currents. The signal conductors and the current conductor, i.e. the respective signal and current paths, are routed over the electrical connector being a non-coaxial connector. Within the electrical connector in the first part the corresponding first connection conductors and the second connection conductor run in parallel over a certain distance. The current conductor generates a rather strong magnetic field around it, if the ablation current is flowing through the second connection conductor, wherein this magnetic field generates an induced signal, i.e. an induced voltage, in the loop formed by the first connection conductors. The strength of this induced signal depends on the strength of the current through the second connection conductor in the first part and the geometry of the loop formed by the first connection conductors in the first part. In particular, the strength of the induced signal may depend on the distance of the first connection conductors to the second connection conductor in the first part, the orientation of the first connection conductors and the distance between the first connection conductors. The first connection conductors in the first part may be arranged such that the induced signal is minimized. However, because of connector construction constraints the straight first connection conductors in the first part, in particular, the signal pins, cannot be perfectly placed such that the interference cannot be completely eliminated. The electrical connector comprises therefore a second part, i.e. the inductive disturbance reduction device, in which substantially the same interference is induced in the signal to be transmitted via the signal conductors, but with an opposite polarity, in order to cancel out the induced signal generated in the first part. Thus, the first conductors in the second part preferentially form a further loop picking up the same interference, but with opposite polarity, in order to substantially cancel the total induced interference.

The first part can form a male part and the second part can form a female part of the electrical connector being a non-coaxial connector. The connection of the male and female parts is preferentially seamless. The second part of the electrical connector comprises the compensation layout, i.e. a layout of first conductors and a second conductor being such that the voltage induced in the first part is compensated by the voltage induced in the second part. In order to produce the second part, the first conductors and the second conductor can be arranged and formed as desired and then overmolded. This allows arranging the first conductors and the second conductors in the second part in any desired spatial configuration, even in any three-dimensional configuration, in order to realize, for instance, a desired twist of the conductors.

For example, a mold can be provided comprising shaped channels for receiving wires to be bent as desired. For bending the wires they can be inserted into the channels of the mold. The mold may be openable such that the bent wires can be withdrawn from the mold, wherein then the bent wires can be overmolded for producing the second part. The mold can also comprise stiff plastic tubes made of plastic having a melting temperature being lower than the melting temperature of a plastic used for overmolding. Wires can be fed into the stiff plastic tubes, in order to produce the desired arrangement of the wires. The plastic with the higher melting temperature can then be overmolded on the mold with the plastic tubes, in order to melt the two plastics together around the wires.

In an embodiment a printed circuit board with the desired layout of conductors forming the second part, i.e. the inductive disturbance reduction device, of the electrical connector can directly be soldered onto the first part of the electrical connector. The printed circuit board may comprise a trace for being connected to the second connection conductor of the first part and to a first conductor of a cable for transmitting RF ablation current, and traces for ultrasound channels, i.e. for being connected with the first connection conductors of the first part and with signal conductors, i.e. first conductors, of a cable transmitting the signals. These traces on the printed circuit board are preferentially arranged such that the induced signal in the loop formed by the signal connection traces is the same, but with opposite polarity, as the signal induced in the first part. Since the traces can be relatively freely arranged on the printed circuit board, the first connection conductors and the second connection conductor, in particular, the corresponding pins in the first part, can be arranged freely, wherein the resulting interference in the first part can still be compensated by arranging the traces on the printed circuit board accordingly. Thus, the first part may comprise any pin layout. If a flexible foil is used instead of a printed circuit board, the freedom of bending of the flexible foil is preferentially limited, in particular, by attaching the flexible foil to a rigid or semi-rigid element like a handset of a catheter.

The electrical connector is preferentially a non-coaxial connector for applications in which sensitive signal channels are routed over the same connector as high current signals. For instance, the electrical connector can be adapted to be used in applications using ablation catheters or ablation needles having an integrated sensor like an electric or electromagnetic sensor.

In an embodiment the first conductors and the second conductor of the inductive disturbance reduction device can have any form, i.e. they can have any positions and/or shapes in three-dimensional space, which allows for a reduction, particularly for a cancelling, of the inductive disturbance of the signal to be transmitted via the first connection conductors of the electrical connector, which is caused when RF ablation current usable for ablating tissue flows through the second connection conductor of the electrical connector. For instance, if in an embodiment the first conductors of the inductive disturbance reduction device invert or reverse their positions relative to the second conductor, the inversion or reversion location does not need to be at a middle point of the entire signal path defined by the electrical conductors transmitting the sensing signals like the first connection conductors of the electrical connector, the first conductors of the inductive disturbance reduction device and further conductors, to which the first connection conductors of the electrical connector and the first conductors of the inductive disturbance reduction device are connected. Moreover, in an embodiment the three-dimensional arrangement of the first conductors of the inductive disturbance device and the first connection conductors of the electrical connector is not symmetric with respect to an inversion or reversion location, i.e. in FIG. 3 the conductors 27, 28, 29 of the inductive disturbance device 18 may not have straight portions having distances to each other, which correspond to distances of the conductors 24, 25, 26 in the first part 17 of the electrical connector. For instance, the straight portions of the conductors 27, 28, 29 may have other distances to each other and/or the conductors 27, 28, 29 may be shaped and positioned in three-dimensions in another way such that the inductive disturbance is reduced.

Although in above described embodiments the electrical connector is adapted to connect two signal conductors, i.e. two first conductors 22, 23, of a first cable 20 with two signal conductors, i.e. two first conductors 33, 34, of a second cable 30, in other embodiments the electrical connector can also be adapted to electrically connect more than two pairs of signal conductors with each other.

Although in above described embodiments the electrical connector is configured to electrically connect two signal conductors of a first cable with two signal conductors of a second cable for transmitting ultrasound signals of a single ultrasound sensor via the electrical connector, in other embodiments the electrical connector can be adapted to allow a transmission of signals of several sensors via the electrical connector. The electrical connector can therefore be a multiple signal electrical connector for electrically connecting several signal conductors of a first cable with several signal conductors of a second cable, wherein the several signal conductors transmit signals generated by different sensors like an ultrasound sensor, an electrical activation sensor, a thermocouple sensor, a pressure sensor, et cetera. The electrical connector can also be used to transmit sensing signals from several sensors of the same type, for instance, for transmitting sensing signals generated by multiple ultrasound transducers. In an embodiment the electrical connector comprises up to fourteen first connection conductors, in particular, in order to use the electrical connector for transmitting several sensor signals from several sensors. For instance, the electrical connector may be adapted to electrically connect a cardiac ablation monitoring catheter comprising multiple sensors integrated into the tip of the cardiac ablation monitoring catheter such as ultrasound sensors, thermocouples, electrical activity monitoring electrodes, et cetera. Thus, instead of using a corresponding multi-coaxial connector for electrically connecting the cardiac ablation monitoring catheter comprising the multiple sensors, a technically less complex electrical connector can be used, which is low in price and which may even be used as disposable electrical connector, which may be permanently connected to a disposable cable or another disposable electrical component.

Although in above described embodiments electrical conductors are arranged on a single printed circuit board or a single flexible foil, i.e. in a single plane, in other embodiments the electrical conductors can also be arranged in multiple planes by arranging several electrical conductors on several layers of printed circuit boards or flexible foils.

Although in above described embodiments the second connection conductor of the first part and the second conductor of the second part are straight conductors, in other embodiments the second connection conductor of the first part and/or the second conductor of the second part can also be bent. For instance, in the second part of the electrical connector the second conductor may be bent, in order to induce a voltage in the first conductors of the second part of the electrical connector, which at least partly compensates the voltage induced in the first connection conductors of the first part.

Although in above described embodiments the first conductors of the inductive disturbance reduction device are adapted to transmit ultrasound sensing signals, in other embodiments the first conductors of the inductive disturbance reduction device can be adapted to transmit other kinds of sensing signals like temperature sensing signals, sensing signals generated by electrically sensing tissue, et cetera.

The inductive disturbance reduction device can also be a component not being integrated in an electrical connector, but, for instance, a component integrated with a cable or a separate device to be directly or indirectly electrically connected to an electrical connector. Also in this case the inductive disturbance reduction device may comprise a printed circuit board or a flexible foil, wherein the inductive disturbance reduction device is rigid or at least semi-rigid, in order to provide a geometry of the conductors within the inductive disturbance reduction device, which allows for at least partially canceling out the induced voltages generated in the electrical connector.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention relates to an inductive disturbance reduction device for reducing an inductive disturbance of a signal like an ultrasound signal to be transmitted via first connection conductors of an electrical connector, which is caused when ablation current flows through a second connection conductor of the electrical connector. The inductive disturbance reduction device is adapted to induce a voltage, which at least partly compensates a voltage induced in the electrical connector, in order to reduce the inductive disturbance in the signals to be transmitted via the first connection conductors of the electrical connector. Since the inductive disturbance is reduced, a high quality electrical connection can be provided, without necessarily using, for instance, a technically relatively complex and expensive coaxial connector. The inductive disturbance reduction device may be integrated, for instance, in a part of the electrical connector or in a cable.

The invention claimed is:

1. An inductive disturbance reduction device for reducing an inductive disturbance of signals transmitted via first connection conductors of an electrical connector, the inductive disturbance being caused when radio frequency ablation current usable for ablating tissue flows through a second connection conductor of the electrical connector, wherein the electrical connector is adapted to electrically connect an ablation catheter with a radio frequency ablation current source, the inductive disturbance reduction device comprising:

first compensation conductors adapted to be electrically connected to the first connection conductors of the electrical connector, the first compensation conductors of the inductive disturbance reduction device being adapted to transmit the signals, and a second compensation conductor adapted to be electrically connected to the second connection conductor of the electrical connector, the second compensation conductor of the inductive disturbance reduction device being adapted to transmit the radio frequency ablation current, wherein:

the first compensation conductors and the second compensation conductor of the inductive disturbance reduction device are arranged such that a compensation voltage is induced in the first compensation conductors of the inductive disturbance reduction device when the radio frequency ablation current flows through the second compensation conductor of the inductive disturbance reduction device; and the compensation voltage induced in the first compensation conductors of the inductive disturbance reduction device at least partly compensates a connection voltage, having a polarity opposite a polarity of the compensation voltage, induced in the first connection conductors of the electrical connector when the radio frequency ablation current flows through the second connection conductor of the electrical connector.

2. The inductive disturbance reduction device as recited in claim 1, wherein one of the first connection conductors of the electrical connector is closer to the second connection conductor of the electrical connector than another of the first connection conductors of the electrical connector.

3. The inductive disturbance reduction device as recited in claim 2, wherein each of the first connection conductors and the second connection conductor of the electrical connector is at least partly straight, and each of the first compensation conductors and the second compensation conductor of the inductive disturbance reduction device is at least partly straight.

4. The inductive disturbance reduction device as recited in claim 3, wherein the one of the first connection conductors of the electrical connector is closer to the at least partly straight part of the second connection conductor of the electrical connector, and one of the first compensation conductors is farther away from the at least partly straight part of the second compensation conductor of the inductive disturbance reduction device than the at least partly straight part of another one of first compensation conductors of the first compensation conductors of the inductive disturbance reduction device.

5. The inductive disturbance reduction device as recited in claim 4, wherein the at least partly straight part of the another one of the first compensation conductors that is farther away from the at least partly straight part of the second compensation conductor is electrically connected to the one of the first connection conductors that is closer to the at least partly straight part of the second connection conductor of the electrical connector.

6. The inductive disturbance reduction device as recited in claim 2, wherein one of the first compensation conductors of the inductive disturbance reduction device, which is farther away from the second compensation conductor, is adapted to be electrically connected to the one of the first connection conductors of the electrical connector, which is closer to the second connection conductor of the electrical connector than the another of the first connection conductors.

7. The inductive disturbance reduction device as recited in claim 1, wherein the inductive disturbance reduction device is integrated in or connected to the electrical connector.

8. The inductive disturbance reduction device as recited in claim 7, wherein the electrical connector comprises separable first and second parts, the second part including the first compensation conductors and the second compensation conductor.

9. The inductive disturbance reduction device as recited in claim 1, wherein the inductive disturbance reduction device is integrated with a cable comprising first cable conductors for transmitting the signals to the first compensation conductors and a second cable conductor for transmitting the radio frequency ablation current to the second compensation conductor, wherein the cable is adapted to be connected to the electrical connector.

10. The inductive disturbance reduction device as recited in claim 1, wherein the first compensation conductors and the second compensation conductor of the inductive disturbance reduction device are overmolded.

11. The inductive disturbance reduction device as recited in claim 1, further comprising a printed circuit board or a flexible foil on which the first compensation conductors of the inductive disturbance reduction device and the second compensation conductor of the inductive disturbance reduction device are arranged.

12. An electrical connector being adapted to electrically connect an ablation catheter with a radio frequency ablation current source, the electrical connector comprising:

a first part comprising:
first connection conductors for transmitting signals;
a second connection conductor for transmitting a radio frequency ablation current usable for ablating tissue, wherein a first voltage is induced in the first connection conductors when the radio frequency ablation current flows through the second connection conductor; and a second part comprising:
first compensation conductors adapted to be electrically connected to the first connection conductors, the first compensation conductors being adapted to transmit the signals, and a second compensation conductor adapted to be electrically connected to the second connection conductor, the second compensation conductor being adapted to transmit the radio frequency ablation current, wherein: the first compensation conductors and the second compensation conductor of the second part are arranged such that a second voltage is induced in the first compensation conductors when the radio frequency ablation current flows through the second compensation conductor; and the second voltage has a polarity opposite a polarity of the first voltage, at least partly canceling the first voltage induced in the first connection conductors of the first part when the radio frequency ablation current flows through the second connection conductor of the first part.

13. A cable comprising:

first cable conductors for transmitting signals,
a second cable conductor for transmitting radio frequency ablation current usable for ablating tissue, wherein the cable is adapted to be connected to an electrical connector to electrically connect an ablation catheter with a radio frequency ablation current source and wherein the electrical connector comprises first connection conductors for electrically connecting the first cable conductors of the cable for transmitting the signals and a second connection conductor for electrically connecting the second cable conductor of the cable for transmitting the radio frequency ablation current, wherein a first voltage is induced in the first connection conductors when the radio frequency ablation current flows through the second connection conductor, and an inductive disturbance reduction device, comprising:
first compensation conductors adapted to be electrically connected to the first connection conductors of the electrical connector, the first compensation conductors of the inductive disturbance reduction device being adapted to transmit the signals received from the first cable conductors, and a second compensation conductor adapted to be electrically connected to the second connection conductor of the electrical connector, the second compensation conductor of the inductive disturbance reduction device being adapted to transmit the radio frequency ablation current received from the second cable conductor, wherein:

the first compensation conductors and the second compensation conductor of the inductive disturbance reduction device are arranged such that a second voltage is induced in the first compensation conductors of the inductive disturbance reduction device when the radio frequency ablation current flows through the second compensation conductor of the inductive disturbance reduction device; and the second voltage induced in the first conductors of the inductive disturbance reduction device at least partly compensates a first voltage, having a polarity opposite a polarity of the second voltage, induced in the first connection conductors of the electrical connector when the radio frequency ablation current flows through the second connection conductor of the electrical connector.

14. A manufacturing apparatus for manufacturing the inductive disturbance reduction device as recited in claim 1 the manufacturing apparatus comprising:

an electrical conductor providing unit for providing the first compensation conductors of the inductive disturbance reduction device for being electrically connected to the first connection conductors of the electrical connector for transmitting the signals and the second compensation conductor of the inductive disturbance reduction device for being electrically connected to the second connection conductor of the electrical connector for transmitting the radio frequency ablation current; and an arranging unit for arranging the first compensation conductors and the second compensation conductor of the inductive disturbance reduction device such that in the first compensation conductors of the inductive disturbance reduction device the compensation voltage is induced, when the radio frequency ablation current flows through the second compensation conductor of the inductive disturbance reduction device, which at least partly compensates the connection voltage induced in the first connection conductors of the electrical connector, when the radio frequency ablation current flows through the second connection conductor of the electrical connector.

* * * * *